United States Patent
Brastaad et al.

(10) Patent No.: US 10,640,823 B2
(45) Date of Patent: May 5, 2020

(54) DETECTING GENETIC COPY NUMBER VARIATION

(71) Applicant: Quest Diagnostics Investments Incorporated, Wilmington, DE (US)

(72) Inventors: Corey Brastaad, Southampton, MA (US); Christopher D. Elzinga, Newton, MA (US); Mingsheng Zhang, Belmont, MA (US); Matthew C. Evans, Shrewsbury, MA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 969 days.

(21) Appl. No.: 14/794,755

(22) Filed: Jul. 8, 2015

(65) Prior Publication Data

US 2017/0009287 A1 Jan. 12, 2017

(51) Int. Cl.
*C12Q 1/6874* (2018.01)
*C12Q 1/6827* (2018.01)
*C12Q 1/6869* (2018.01)

(52) U.S. Cl.
CPC ......... *C12Q 1/6874* (2013.01); *C12Q 1/6827* (2013.01); *C12Q 1/6869* (2013.01)

(58) Field of Classification Search
None
See application file for complete search history.

(56) References Cited

PUBLICATIONS

Smith et al. Highly-multiplexed barcode sequencing: an efficient method for parallel analysis of pooled samples, Nucleic Acids Res. Jul. 2010; 38(13): e142. Published online May 11, 2010. doi: 10.1093/nar/gkq368.*

Kallioniemi et al., Comparative Genomic Hybridization: A Rapid New Method for Detecting and Mapping DNA Amplification in Tumors, 1993 Seminars in Cancer Bio. 4(1): 41-46.

Fisher et al., A Scalable, Fully Automated Process for Construction of Sequence-Ready Human Exome Targeted Capture Libraries, 2011 Genome Biology 1281, available at http://www.ncbi.nlm.nih.gov/pmc/articles/PMC3091298.

* cited by examiner

*Primary Examiner* — Joseph Woitach
(74) *Attorney, Agent, or Firm* — Jon E. Gordon; Haug Partners LLP

(57) ABSTRACT

Embodiments of the invention include systems, apparatus, and methods for detecting copy number variation (CNV) in the genomes of one or more patients. Samples of DNA may be taken from several patients, and then sections of the patients' DNA may be sequenced, e.g., through a process that may include, for each patient, one or more of: purifying, concentrating, fragmenting, labeling, filtering, and amplifying that patient's DNA. Fragments from several patients may be pooled, and the fragments in the pool may be sequenced.

The sequencing data is then subjected to analysis, which includes several normalization steps. The normalized data are then examined to identify CNV, which is reported.

12 Claims, 8 Drawing Sheets

Specification includes a Sequence Listing.

Normal Patient - No CNV Detected

DETECTING GENETIC COPY NUMBER VARIATION

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records, but otherwise reserves all copyrights whatsoever.

BACKGROUND

An organism's genes, in the form of deoxyribonucleic acid (DNA), encode all of that organism's proteins and functional RNA. The organism's genes provide the information that is needed to build and maintain its cells and to reproduce. Each cell of the organism includes a full copy of the organism's genome, and each time a cell replicates itself, it creates a copy of the whole genome.

But copying DNA is sometimes imperfect, and imperfect copying of DNA can be a source of genetic mutation. Errors introduced in copying are one source of mutation. And while mutation makes evolution possible, many mutations are known also to be associated with disease or an increased risk of it.

One type of error in duplication is omission of a segment of DNA. Another type of error is making multiple copies of the same segment of DNA. Both kinds of errors can be referred to as copy number variation (CNV).

Associations can be found between CNV and certain conditions, including, e.g., health or medical conditions, including some diseases. But finding an association between a specific CNV and a specific condition requires first finding CNV in the genomes of people who have the condition. Once the association is established, moreover, it can be used for diagnostic purposes, but that, too, requires finding the CNV in the genome of a person who is suspected of having the condition.

Some procedures are known for finding CNV in individuals. For example, in fluorescence in situ hybridization (FISH), a fluorescent probe includes and oligonucleotide that is designed to complement only one or more specific parts of a chromosome. Duplications or deletions could be found by identifying regions of greater or lesser fluorescence respectively. But one drawback of FISH is its low resolution, being unsuitable for detecting regions shorter than 5-10 Mb. FISH is described in, e.g., Kallioniemi et al., *Comparative Genomic Hybridization: A Rapid New Method for Detecting and Mapping DNA Amplification In Tumors,* 1993 SEMINARS IN CANCER BIO. 4(1):41-46.

Another technique for detecting CNV is array-Comparative Genomic Hybridization (aCGH). In this assay, DNA from a reference sample is labeled with a fluorophore, and DNA from a patient sample is labeled with a different fluorophore. The labeled samples are then used as probes that are cohybridized competitively onto nucleic acid targets. aCGH also suffers from limited resolution, being unable to detect CNV of regions smaller than about 40 kb.

Other approaches to measuring dosage may involve DNA sequencing, but directly sequencing from raw DNA is not practical. Sequencing large numbers of short segments of DNA (e.g., 150-200 bases) in large numbers is practical but introduces new difficulties, such as the bias and/or sampling error resulting from DNA amplification and the problem of using short subsequences to detect abnormal copying or deletion of potentially long sequences.

It would therefore be advantageous to develop techniques for detecting CNV that could be based on sequencing short segments of DNA while overcoming the obstacles inherent in using this kind of sequencing.

BRIEF SUMMARY

Embodiments of the invention include apparatus, systems, and methods of detecting variations in the number of copies of genetic subsequences within the genome of an organism. The invention is illustrated by embodiments that are used to examine human genetic material in a medical context, which is why there are many references herein to patients, but this is only for example. Persons having skill in the art will appreciate that the invention applies equally to detecting copy number variations in genetic sequences from any organism.

According to embodiments of the invention, samples of genetic material, including DNA, may be taken from several patients. Sections of the patients' DNA may then be sequenced, e.g., through a process that includes, for each patient, purifying, concentrating, and fragmenting that patient's DNA. Each fragment may receive a molecular label that identifies the patient from whom the DNA was received and the DNA may otherwise be modified in preparation for sequencing (e.g., through one or more steps that may include one or more of: filtration, amplification, and modification such as to attach primers to the fragments).

The fragments from several patients may be pooled, and the pool may include, e.g., one or more controls that comprise known genetic material. The fragments in the pool may then be sequenced, and the results of the sequencing may be stored, e.g., as one or more computer files.

The results may then be processed, e.g., by one or more computer systems, to identify possible copy number variations in the patients from whom the samples were taken. For example, according to embodiments of the invention, the sequences may be demultiplexed to identify the respective patients whose DNA each sequence represents. Each patient's samples may then be aligned to a reference genome, and coverage for each base pair in each region of interest on the patient's genome may then determined. From the base pair coverage, the coverage of one or more subunits of the patient's genome may then be determined. For example, in connection with an embodiment of the invention, the coverage of multiple exons may be determined.

According to embodiments of the invention, the measurements of the coverage may then go through one or more steps of normalization. For example, according to an embodiment of the invention, the mean coverage of one or more amplicons known to be on autosomes may be compared to the mean coverage of one or more amplicons known to be on the X chromosome to provide a rough estimate of the number of X chromosomes (viz., one or two) in the patient's karyotype. If the patient is determined to have only one X chromosome, normalization may include doubling the coverage of all amplicons known to come from the X chromosome. Following normalization, reference values may be calculated for each amplicon, and CNV may be detected by comparing actual coverage values for each patient's amplicons with the calculated reference values.

According to an embodiment of the invention, a method is provided of detecting copy number variation (CNV) in the DNA of a plurality of patients. The method comprises receiving a plurality of samples, each sample containing DNA from a single patient, and from each sample, generating a plurality of fragments of DNA. The method also comprises barcoding each of the fragments with an identifier that uniquely identifies the respective patient from whom the DNA was received, pooling the plurality of samples into a DNA library, and subjecting the DNA library to one or more stages of filtering to increase the relative concentration of fragments within a plurality of selected regions of interest.

The method further comprises producing sequencing data for the plurality of patients by sequencing the filtered DNA library, demultiplexing the sequencing data, and, for each patient, generating coverage data by identifying, for each of the regions of interest, coverage of each region of interest in the sequencing data. The method comprises generating normalized coverage data from the coverage data and generating reference coverage, common to all samples, for each region of interest, the generation of the reference coverage being based upon the normalized coverage data. The method also comprises automatically detecting CNV for at least one subsequence of at least one of the regions of interest of at least one of the patients based upon comparing the reference coverage to the normalized coverage data and providing output that identifies the patient, the subsequence, and the CNV.

According to embodiments of the invention, generating normalized coverage data from the coverage data comprises generating raw coverage data for each patient by at least generating an estimate of the number of the patient's X chromosomes based on the coverage data and scaling the patient's coverage of at least one region of interest that is known to be X-linked and further comprises generating normalized coverage data from the raw coverage data.

According to an embodiment of the invention, generating the estimate of the number of each patient's X chromosomes occurs without reference to any demographic information about the respective patient and without reference to any information about the respective patient's phenotype. Alternatively, according to an embodiment of the invention, the method comprises, for each patient, generating a second estimate of the number of the patient's X chromosomes based on the normalized coverage data and also comprises revising the normalized coverage data based on the second estimates. In an embodiment of the invention, generating the second estimate of the number of each patient's X chromosomes occurs without reference to any demographic information about the respective patient and without reference to any information about the respective patient's phenotype.

According to embodiments of the invention, the coverage data comprises per-base coverage for each region of interest within the sequencing data; generating raw coverage data comprises scaling the patient's per-base coverage of the at least one region of interest that is known to be X-linked; the normalized coverage data comprises per-base coverage; the reference coverage comprises per-base coverage for each position within each region of interest; and automatically detecting CNV is based upon the per-base reference coverage and the normalized coverage data.

According to embodiments of the invention, each region of interest corresponds respectively to exactly one exon and contains that exon. In an embodiment of the invention, the method comprises automatically detecting CNV for a plurality of adjacent exons within a gene of a patient, each of the adjacent exons having the same CNV and automatically rolling up the CNV of the adjacent exons. Further, in an embodiment, the method comprises automatically detecting CNV for all exons within a gene of a patient, each of the exons within the gene having the same CNV, and automatically rolling up the CNV of the exons within the gene into a single CNV for the gene. According to embodiments of the invention, the method comprises subjecting the DNA library to one or more stages of amplification, such that each region of interest is an amplicon.

According to embodiments of the invention, the coverage data comprises per-base coverage for each region of interest within the sequencing data; the normalized coverage data comprises per-base coverage; the reference coverage comprises per-base coverage for each position within each region of interest; and automatically detecting CNV is based upon the per-base reference coverage and the normalized coverage data.

BRIEF DESCRIPTION OF THE DRAWINGS

The invention is illustrated in the figures of the accompanying drawings, which are meant to be exemplary and not limiting, and in which like references are intended to refer to like or corresponding things.

DETAILED DESCRIPTION OF THE PREFERRED EMBODIMENTS

Obtaining DNA Samples

"DNA sequencing" refers to identifying the sequence of nucleotides that make up a DNA molecule. ("Sequence", as used here, may refer either to the arrangement of nucleotides within a DNA molecule or part of it or to the representation of that arrangement that is produced as a result of sequencing. The precise meaning of any occurrence of "sequence" should be clear from context.) In connection with embodiments of the invention, DNA sequencing may begin with obtaining specimens that include a patient's DNA. In an embodiment of the invention, the specimens may be, e.g., blood drawn from the patient into a vial. It will be appreciated that DNA may be found in varied tissues and fluids, and other material may therefore be collected in connection with alternative embodiments of the invention.

Shearing

According to an embodiment of the invention, fragments of the patient's DNA may be sequenced, e.g., automatically by a commercially available sequencing platform such as the MiSeq® Personal Sequencer. But such a sequencer may be able to read only relatively short sequences, e.g., depending on the platform, 150-300 base pairs. It may therefore be necessary to break genomic DNA into fragments that are short enough to be sequenced reliably.

Figure 1:
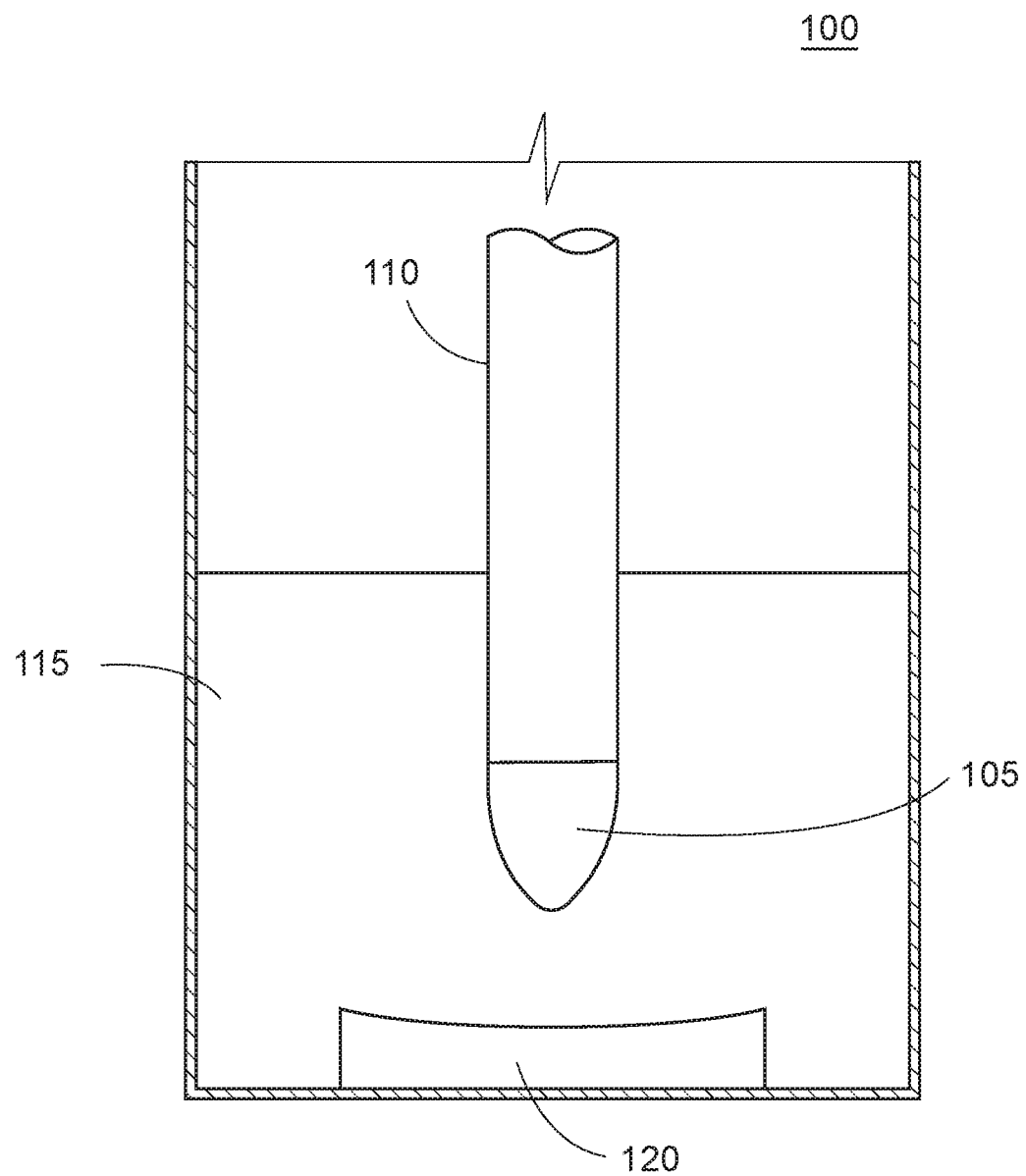
FIG. 1 depicts schematically a device usable for acoustically shearing DNA into fragments in connection with an embodiment of the invention.

According to an embodiment of the invention, DNA in patient samples may be sheared acoustically, e.g., using a device such as those provided by Covaris®. FIG. 1 depicts schematically elements of such a device 100. An amount from the patient sample 105 may be placed in a glass tube 110, and the tube 110 may be placed in a chilled water bath 115. (Although FIG. 1 depicts only one tube 110, devices known in the art may receive multiple tubes at one time (not pictured).)

The depicted device 100 includes a convex transducer 120, which generates sound waves that are focused on the bottom of the tube 110, forming many small bubbles on the inside of the tube 110. The collapse of these bubbles creates relatively high velocity bursts that mechanically shear DNA.

According to an embodiment of the invention, a consistent barrage of AFA energy each time DNA is sheared generates DNA fragments that are similar in size across sample treatments. For example, according to an embodiment of the invention, the target size for DNA fragments is 200 base pairs. Techniques for varying the expected fragment size are known in the art.

Concentration

After shearing of the DNA, a sample may still contain material other than DNA, such as cellular debris and proteins. Some of this material may interfere with further preparation of material for sequencing or sequencing itself. Thus, according to an embodiment of the invention, shearing may be followed by one or more (typically more) rounds of sample cleanup.

For example, it is known in the art to use solid-phase reversible immobilization (SPRI) beads to attract fragments of DNA in solution. An example of the use of SPRI beads may be found, e.g., in Fisher et al, *A Scalable, Fully Automated Process for Construction of Sequence-Ready Human Exome Targeted Capture Libraries*, 2011 GENOME BIOLOGY 1281, doi: 10.1186/gb-2011-12-1-r1.

In summary, SPRI beads may be made, e.g., of polystyrene covered by a layer of magnetite and coated with carboxyl molecules. SPRI beads may be added to a solution that contains DNA fragments. If the solution is then adjusted to have the proper concentrations of polyethylene glycol (PEG) and salt (NaCl), DNA will bind to the beads, which may then be magnetically separated from the supernatant. The beads may then be washed one or more times, e.g., with ethanol. After washing, DNA may be eluted from the beads, e.g., with a small amount of a buffer such as 0.1× Tris-Cl/ EDTA (TE). (Details of the procedure, including, e.g., suitable concentrations of PEG and NaCl, are available in the publication and are otherwise well known in the art.)

End Repair (Blunting)

Figure 2A:
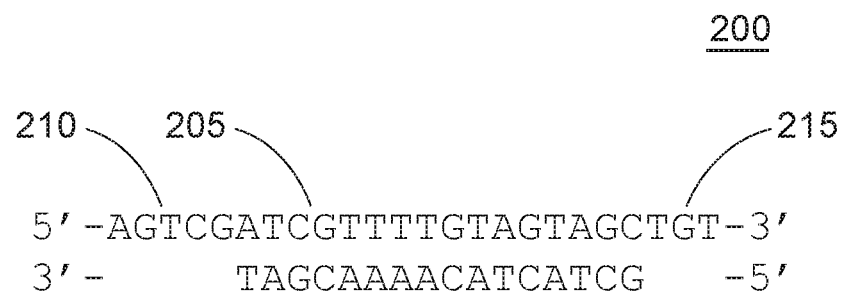
FIG. 2a depicts a fragment of DNA with overhangs. The depicted strands are depicted in SEQ ID NO: 1 and SEQ ID NO. 2.

A DNA molecule consists of two complementary strands of nucleotides. Mechanically shearing DNA into appropriately-sized fragments in connection with an embodiment of the invention may leave the ends of the segments with overhangs, i.e., one or more unpaired nucleotides at the end of a DNA strand. FIG. 2a depicts a DNA fragment 200 in which one of the strands 205 has overhangs at the 5' end 210 and the 3' end 215. Some DNA sequencing techniques, including techniques that may be used in connection with embodiments of the invention, require that DNA fragments be ligated to adapters, and ligating adapters to fragments may require that the fragments have blunt ends.

Figure 2B:
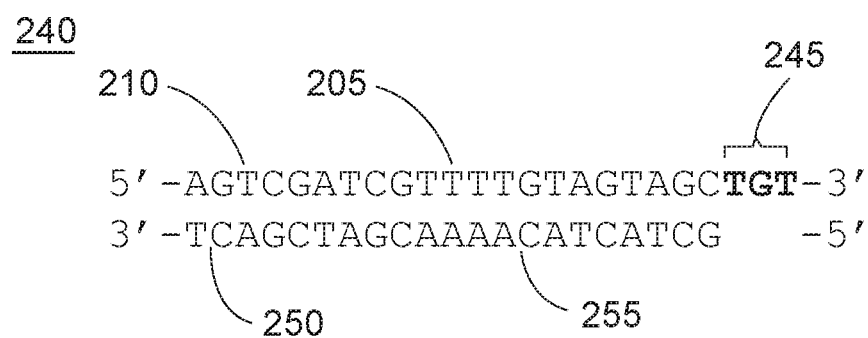
FIG. 2b depicts the fragment of FIG. 2a following blunting of the ends. The depicted strands, following blunting, are depicted in SEQ ID NO: 1 and SEQ ID NO 3.

Blunting of DNA fragments may be accomplished, e.g., through one or more techniques known to the art, such as enzymatic repair of the ends. An enzyme used for this purpose may be, e.g., a polymerase that has 5'→3' polymerase activity and 3'→5' exonuclease activity, and suitable enzymes will be known to those skilled in the art and are commercially available. FIG. 2b depicts a DNA fragment 240 such as might result from blunting the fragment 200 that FIG. 2a depicts: the three overhanging nucleotides 245 have been removed from the 3' end 215 of one strand 205, and the 3' end 250 of the other strand 255 has been extended to complement the 5' end 210 of the first strand 205.

Cleanup may follow blunting, according to an embodiment of the invention, and this cleanup may include, e.g., mixing the samples with SPRI beads in a solution containing PEG and salt, washing the beads, and then eluting the DNA from the beads, as described previously.

Adapter Ligation and Cleanup

As described previously, in embodiments of the invention, sequencing of DNA fragments may be done, e.g., by a sequencer such as sold commercially by MiSeq®. Within a MiSeq® sequencer, a flow cell may require that a fragment to be sequenced begin and end with adapters that complement oligonucleotides on the surface of the flow cell. Thus, preparation of a sample for sequencing according to an embodiment of the invention may include ligating adapters to the ends of the fragments in the sample.

For example, according to an embodiment of the invention, two adapters may be used: P5 and P7. These adapters may be chosen, e.g., for compatibility with particular sequencing apparatus. In an embodiment, both adapters are blunt ended and not 5' phosphorylated. Because blunting causes 5' phosphorylation of the patient DNA fragments, they can bind to the adapters and to each other. The P5 and P7 adapters are not 5' phosphorylated, though, so they cannot bind to each other, but they can bind to fragments in one of three combinations: P5-fragment-P7, P5-fragment-P5, and P7-fragment-P7.

In this ligation reaction, according to an embodiment of the invention, the molar ratios of the two adapters may be equal, and both may exceed the molar ratio of the fragments. This balance means that roughly half of all ligation products are the preferred species: P5-fragment-P7.

One or both adapters may include patient-specific subsequences of nucleotides. In connection with embodiments of the invention, each sequencing run may be expensive, but the run may produce tens or hundreds of millions of sequences. This sequencing information may be more redundant than needed for reliable analysis. It may therefore be more cost-effective to analyze DNA from multiple patients in a single run, if possible.

Patient-specific adapters may be used, e.g., to realize such cost efficiency. In connection with embodiments of the invention, samples from multiple patients may be pooled and sequenced together, and this pooling may be called "multiplexing". After a run, as described below, individual sequences can be associated with the respective correct patients the their respective patient-specific subsequences through a process called "demultiplexing".

For example, according to an embodiment of the invention, the P5 adapter contains the molecular identification (MID) sequences used to identify each patient sample. (MID sequences may also be called "barcodes", and attaching them to fragments in a patient sample may be called "barcoding" the fragments in the sample, or, for short, called simply barcoding the sample.) In an embodiment of the invention, barcodes may be six nucleotides long, which means that there are $4^6=4096$ possible MID sequences. To improve error detection, however, in an embodiment of the invention, a set of barcodes may be used in which every barcode differs in at least two positions from every other.

It will be appreciated by those skilled in the art that using longer adapters may lead to more undesirable binding, such as daisy chaining and other off-target binding, during subsequent steps in preparation for binding. In embodiments of the invention, only part of each adapter may be ligated to the fragments, with the expectation that the remaining parts will be added in a subsequent step. In such an embodiment, the part of the P5 adapter ligated here will include a barcode, if any is used.

After adapter ligation, the samples may be cleaned, e.g., as previously described.

Nick Repair

DNA shearing and adapter ligation of the adapters may leave nicks in the DNA. A "nick" in this context is a break in one strand of a DNA molecule such that no phosphodiester bond connects adjacent nucleotides. The nucleotides maintain their relative positions, however, because of their bindings to the complementary nucleotides on the other strand. Nicks may exist, e.g., because the adapters may not be 5' phosphorylated (otherwise the adapters may ligate to each other).

Nicks may be repaired by enzymes. For example, in connection with an embodiment of the invention, the nicks at the ligation site may be repaired by a DNA polymerase that adds nucleotides at the nick site in the 5'→3' direction, displacing the nicked strand as it progresses along the template strand. (Suitable enzymes are well known in the art.)

After the nick repair reaction, the sample may cleaned, e.g., as previously described.

Pre-hybridization Amplification

To increase the amount of sample material that is hybridized at later stages of the process, and also to increase the ratio of adapted fragments to unbound adapters, in an embodiment of the invention, PCR is used to amplify patient DNA samples. The primers used are complementary to the P5 and P7 adapter sequences, ensuring selective amplification of only the DNA fragments that have been ligated to the adapters. After the amplification, the sample may be cleaned, e.g., as previously described.

Normalization

In an embodiment in which samples from multiple patients are sequenced at the same time, it may be desirable to make sure that the pool includes roughly equivalent concentrations of DNA from each patient. In an exemplary embodiment of the invention, normalization of DNA concentrations comprises first measuring the optical density of each sample and using the result of the measurement to calculate each sample's concentration of DNA. Suitable processes for making this measurement are known to those in the art.

Volumes of each sample may then be added to a common pool. Volumes may be taken from each patient's sample such that the volume taken from each sample is inversely proportional to the respective sample's concentration of DNA, with the result that merging of these specific volumes of DNA generates a pool of approximately equimolar patient DNA samples.

The pooled samples may then be cleaned, e.g., as above, and then concentrated, e.g., by a process that may include desiccation. Suitable processes will be apparent to those skilled in the art.

Library Capture and Target Enrichment

In an embodiment of the invention, only selected regions of the genome may be of interest. In such an embodiment, the presence of DNA from other regions may dilute the coverage of the regions of interest. To prevent this kind of dilution, in an embodiment of the invention, it may be desirable to enrich the pool with fragments from target regions of interest and to remove from the pool adapted fragments that contain portions of the genome that are not intended for sequencing.

Tools and processes are commercially available for selective enrichment of particular targets. For example, in connection with an embodiment of the invention, target enrichment may use SureSelect® products available from Agilent.

Workflows for selective enrichment are known to the art and described, e.g., in appropriate SureSelect® documentation. In summary, the concentrated equimolar pool of patient DNA samples may be added to a hybridization reaction mixture that contains hybridization buffers, which are oligonucleotides that keep adapters from binding each other, and biotinylated RNA baits that are complementary for the sequences of interest. The mixture may be incubated while the biotinylated RNA baits hybridize to the DNA sequence of the region of interest. After incubation, the hybridization mixture may be combined with magnetic beads bound to streptavidin and incubated at room temperature. The magnetic beads may then be used to pull out of solution fragments containing sequence for the region of interest.

Post-hybridization Amplification

At this point, the sample DNA fragments, bound to magnetic beads, may lack full adapter sequences necessary for sequencing the fragments in a flow cell. (This has been disclosed above in the discussion of adapter ligation.) In an embodiment of the invention, the adapters may therefore be completed, e.g., by ligating any missing subsequences to their ends.

The enriched DNA may optionally be amplified, e.g., by PCR using primers that are complementary to the P5 or P7 adapter and also have the remaining necessary sequences. After amplification, the sample pool may be cleaned, e.g., as above, and may then be eluted in water in preparation for a final quantification and sequencing.

It will be appreciated by those skilled in the art that further increases in the relative concentration of DNA fragments from regions of interest may be possible, e.g., by repeated filtering, amplification, or both, possible in alternation. When both filtering and amplification are used, each selected-for region of interest may be called an "amplicon".

Quantification by qPCR

The DNA library at this point according to an embodiment of the invention may be a pool of patient DNA samples that have been fragmented, enriched for the sequence of interest, and ligated to appropriate adapters. In embodiments of the invention, it may be desirable to adjust the amount of the sample that is supplied to a sequencer, e.g., to maximize sequence data output without exceeding any detection saturation threshold of the sequencer. Quantification is a step that can be used to obtain a desirable density of sequence clusters. And according to embodiments of the invention, the relevant quantity is the amount of DNA fragments in the library that are bound to P5 adapters at the 5' ends and P7 adapters at the 3' ends.

According to an embodiment of the invention, quantification is accomplished via the TaqMan® quantitative PCR (qPCR) assay, which is known to the art. This assay takes advantage of the editing function of Taq polymerase in connection with a PCR reaction that uses primers and probes that complement the P5 and P7 adapters. Probes include a fluorophore at one end and a quencher on the other. The quencher quenches the fluorescence produced by the fluorophore, which means that the probe will fluoresce only if the quencher is removed.

If a fragment includes a P5 adapter at one end and a P7 adapter at the other, then a primer will bind to one end, and a probe will bind to the other. During PCR, Taq polymerase will extend the primer towards the probe, building the complementary strand. When the reaction reaches the probe, however, the exonuclease activity of Taq polymerase will degrade the probe, freeing the fluorophore from it.

Freed from the probe, the fluorophore diffuses away from the quencher and becomes able to emit light if excited by a light source that has the correct wavelength. The emitted light is detected and used to generate a plot of fluorescence per cycle of PCR. To determine library loading volume, this fluorescence is then compared to commercially available DNA standards that have been previously compared to libraries with observed cluster densities.

Sequencing

According to embodiments of the invention, a volume of the pooled sample may be placed into a sequencer, and the loading volume may be calculated based on a quantification step such as the one described above. In an embodiment that uses, e.g., the Illumina MiSeq®, the library may be loaded into a well of a reagent cassette.

The details of sequencing may depend, e.g., on the particular platform chosen. The MiSeq, as may be used in connection with embodiments of the invention, operates on the principle of sequencing by synthesis (SBS), as is known in the art. The instrument flushes the library through a flow cell, the inside of which is coated with oligonucleotides that bind to the DNA fragments in the library that have been ligated to the adapters.

Within the flow cell, clusters of DNA are generated from single molecules by isothermal bridge amplification, a process that employs the complementary oligonucleotides bound to the surface of the flow cell with repeated denaturing and extension. After cluster generation, sequencing by synthesis begins. Labeled modified nucleotide triphosphates are applied to the flow cell, with a maximum of one nucleotide incorporation possible per molecule per round of synthesis. Fluorophores on the incorporated nucleotides are then excited by a laser, the emission spectra recorded by the MiSeq, and the modifying moiety on the nucleotide, which had inhibited further synthesis, is cleaved, allowing for addition of the next nucleotide triphosphate. In this manner, fragments are sequenced, first from one end, then from the other.

Data Analysis

It will be appreciated that the result of a sequencing run as described above, according to embodiments of the invention, may include listings of many short sequences (viz., 150-200 bases) from regions of interest that may be hundreds, thousands, or even tens of thousands of bases long, and those sequences may represent DNA from, e.g., dozens of patients. Thus, in an embodiment of the invention, sequencing may be followed by analysis of the resulting data to determine dosages of individual genes in the genomes of the different patients.

Figure 3:
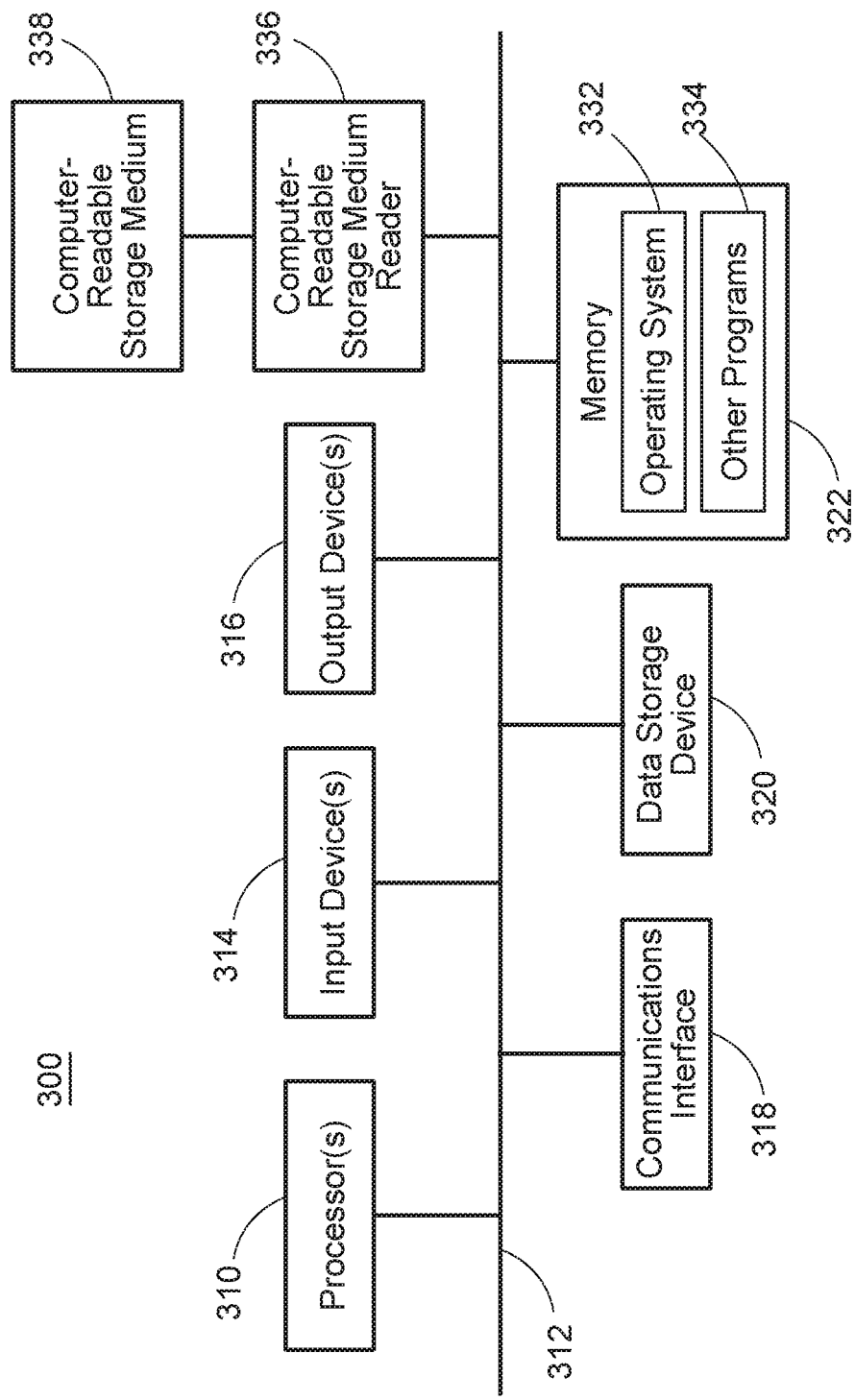
FIG. 3 depicts schematically elements of a computer system such as may be used in connection with an embodiment of the invention.

Data analysis according to embodiments of the invention may be done by one or more computing systems, and the computing systems may interact with each other and other devices (e.g., a sequencer) via one or more computer networks. FIG. 3 depicts an example of one such computer system 300, which includes at least one processor 310, such as, e.g., an Intel or Advanced Micro Devices microprocessor, which may be coupled to a communications channel or bus 312. The computer system 300 further includes at least one input device 314 such as, e.g., a keyboard, mouse, touch pad or screen, or other selection or pointing device, at least one output device 316 such as, e.g., an electronic display device, at least one communications interface 318, at least one data storage device 320 such as a magnetic disk or an optical disk, and memory 322 such as ROM and RAM, each coupled to the communications channel 312. The communications interface 318 may be coupled to a network (not depicted) such as the Internet.

Although the computer system 300 is shown in FIG. 3 to have only a single communications channel 312, a person skilled in the relevant arts will recognize that a computer system may have multiple channels (not depicted), including for example one or more busses, and that such channels may be interconnected, e.g., by one or more bridges. In such a configuration, components depicted in FIG. 3 as connected by a single channel 312 may interoperate, and may thereby be considered to be coupled to one another, despite being directly connected to different communications channels.

One skilled in the art will recognize that, although the data storage device 320 and memory 322 are depicted as different units, the data storage device 320 and memory 322 can be parts of the same unit or units, and that the functions of one can be shared in whole or in part by the other, e.g., as RAM disks, virtual memory, etc. It will also be appreciated that any particular computer may have multiple components of a given type, e.g., processors 310, input devices 314, communications interfaces 318, etc.

The data storage device 320 (FIG. 1) and/or memory 322 may store instructions executable by one or more processors or kinds of processors 310, data, or both. Some groups of instructions, possibly grouped with data, may make up one or more programs, which may include an operating system 332 such as, e.g., Microsoft Windows®, Linux®, Mac OS®, or Unix®. Other programs 334 may be stored instead of or in addition to the operating system. It will be appreciated that a computer system may also be implemented on platforms and operating systems other than those mentioned. Any operating system 332 or other program 334, or any part of either, may be written using one or more programming languages such as, e.g., Java®, C, C++, Objective-C, Visual Basic®, VB.NET®, Perl, Ruby, Python, or other programming languages, possibly using object oriented design and/or coding techniques.

One skilled in the art will recognize that the computer system 300 (FIG. 3) may also include additional components and/or systems, such as network connections, additional memory, additional processors, network interfaces, input/output busses, for example. One skilled in the art will also recognize that the programs and data may be received by and stored in the system in alternative ways. For example, a computer-readable storage medium (CRSM) reader 336, such as, e.g., a magnetic disk drive, magneto-optical drive, optical disk drive, or flash drive, may be coupled to the communications channel 312 for reading from a CRSM 338 such as, e.g., a magnetic disk, a magneto-optical disk, an optical disk, or flash memory. Alternatively, one or more CRSM readers may be coupled to the rest of the computer system 300, e.g., through a network interface (not depicted) or a communications interface 318. In any such configuration, however, the computer system 300 may receive programs and/or data via the CRSM reader 336. Further, it will be appreciated that the term "memory" herein is intended to include various types of suitable data storage media, whether permanent or temporary, including among other things the data storage device 320, the memory 322, and the CSRM 338.

(The term "computer readable storage medium" specifically excludes transitory propagating signals, which should be apparent from the use of the word "storage".)

Figure 4:
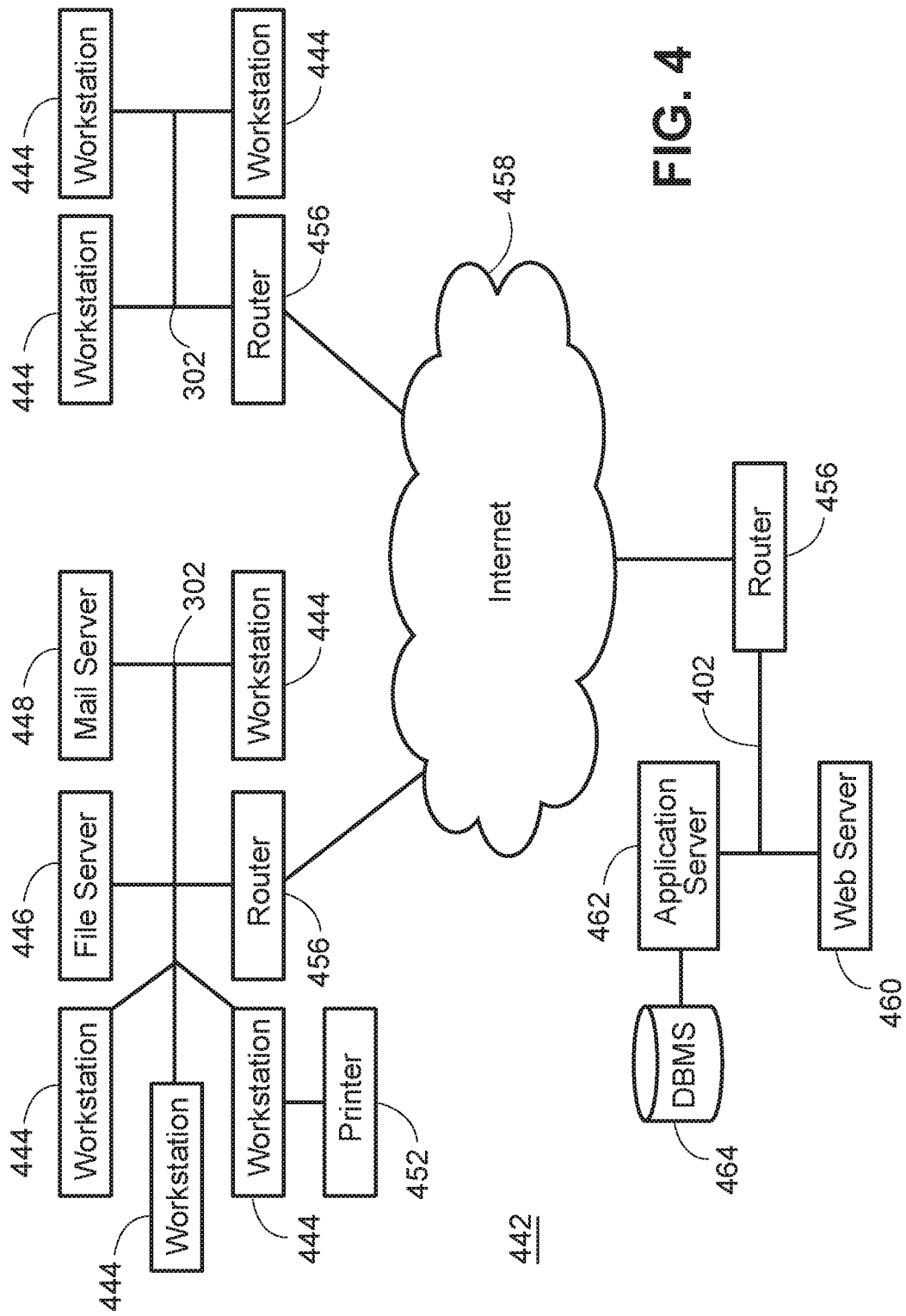
FIG. 4 depicts a network of computer systems and other devices such as may be used in connection with an embodiment of the invention.

Two or more computer systems 300 (FIG. 3) may communicate, e.g., in one or more networks, via, e.g., their respective communications interfaces 318 and/or network interfaces (not depicted). FIG. 4 is a block diagram depicting an example of one such interconnected network 442. Network 442 may, for example, connect one or more workstations 444 with each other and with other computer systems, such as file servers 446 or mail servers 448. A workstation 444 may comprise a computer system 300. The connection may be achieved tangibly, e.g., via Ethernet® or optical cables, or wirelessly, e.g., through use of modulated microwave signals according to the IEEE 802.11 family of standards. A computer workstation 344 or system 300 that participates in the network may send data to another computer workstation system in the network via the network connection.

One use of a network 442 (FIG. 4) is to enable a computer system to provide services to other computer systems, consume services provided by other computer systems, or both. For example, a file server 446 may provide common storage of files for one or more of the workstations 444 on a network 442. A workstation 444 sends data including a request for a file to the file server 446 via the network 442 and the file server 446 may respond by sending the data from the file back to the requesting workstation 444.

Further, a computer system may simultaneously act as a workstation, a server, and/or a client. For example, as depicted in FIG. 4, a workstation 444 is connected to a printer 452. That workstation 444 may allow users of other workstations on the network 442 to use the printer 452, thereby acting as a print server. At the same time, however, a user may be working at the workstation 444 on a document that is stored on the file server 446.

The network 442 (FIG. 4) may be connected to one or more other networks, e.g., via a router 456. A router 456 may also act as a firewall, monitoring and/or restricting the flow of data to and/or from the network 442 as configured to protect the network. A firewall may alternatively be a separate device (not pictured) from the router 456.

An internet may comprise a network of networks 442 (FIG. 4). The term "the Internet" refers to the worldwide network of interconnected, packet-switched data networks that uses the Internet Protocol (IP) to route and transfer data. For example, a client and server on different networks may communicate via the Internet 458, e.g., a workstation 444 may request a World Wide Web document from a Web server 460. The Web server 460 may process the request and pass it to, e.g., an application server 462. The application server 462 may then conduct further processing, which may include, for example, sending data to and/or receiving data from one or more other data sources. Such a data source may include, e.g., other servers on the same computer system 300 or LAN 402, or a different computer system or LAN and/or a database management system ("DBMS") 462.

As will be recognized by those skilled in the relevant art, the terms "workstation," "client," and "server" are used herein to describe a computer's function in a particular context. A workstation may, for example, be a computer that one or more users work with directly, e.g., through a keyboard and monitor directly coupled to the computer system. A computer system that requests a service through a network is often referred to as a client, and a computer system that provides a service is often referred to as a server. But any particular workstation may be indistinguishable in its hardware, configuration, operating system, and/or other software from a client, server, or both.

The terms "client" and "server" may describe programs and running processes instead of or in addition to their application to computer systems described above. Generally, a software client may consume information and/or computational services provided by a software server.

Embodiments of the invention may use the Web or related technologies. Information may be provided to a user in the form of one or more Web pages. A Web page may include one or more of text, sound, still and moving pictures, and other media, and it may be assembled from one or more files and/or other units accessed from one or more servers and/or other computer systems. Some or all of the content of the page may be generated dynamically, e.g., by one or more servers, and some or all of the content of the page may be generated and/or modified dynamically by the user agent (or browser), e.g., through JavaScript and/or other client-side scripting technologies.

The descriptions herein of computers, computer systems, networks, the Internet, and the World Wide Web are intended only for illustration and identification. No such description should be taken to mean that any of those terms is given a meaning other than the ordinary and customary meanings of those terms in the relevant arts.

Figure 5:
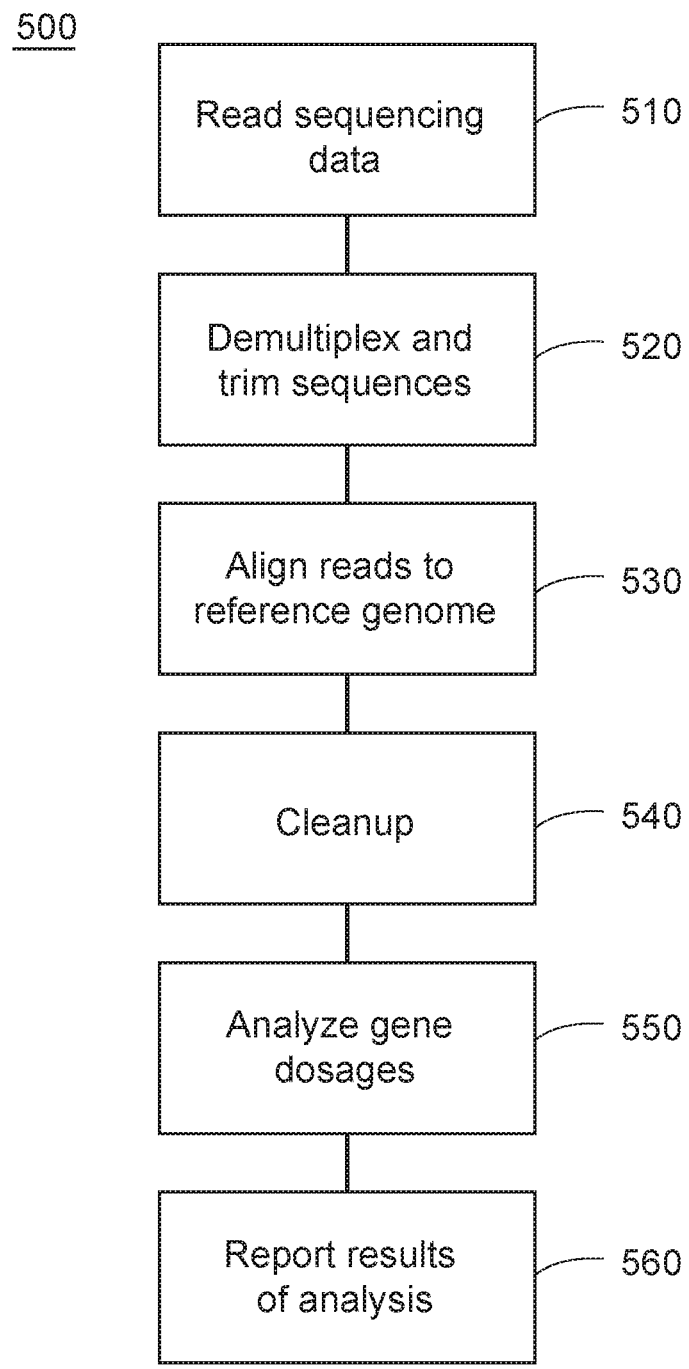
FIG. 5 depicts a flow of analysis of sequencing data according to an embodiment of the invention.

FIG. 5 depicts data analysis 500, at a high level, according to an embodiment of the invention. The process begins in block 510 with importation of the run data for analysis. The run data may be available, e.g., as one or more compressed files in the FASTQ format, which is widely used for transforming sequencing data.

A single run may include results for tens of millions of fragments, however, meaning that the raw data from the run may require several gigabytes of storage. Accordingly, the FASTQ data may be compressed, and importation of the raw data 510 may include, e.g., transferring the compressed files via a computer network from the sequencer to a computer system.

Various tools are known for manipulating and processing genetic sequence information. The invention may be described below in terms of computer systems that run the Linux operating system and various programs within that environment. It will be appreciated, however, that the invention is of more general applicability and not limited to use of any particular operating system or programs.

Following importation 510, the computer system may decompress the file or files (if necessary) and then demultiplex and trim the sequences in block 520. As described above, according to embodiments of the invention, fragments of patient DNA may be ligated to P5 and P7 adapters for sequencing, and the adapters may include barcodes that identify the patients from whom the respective fragments were obtained. In block 520, the sequences are placed in sample-specific FASTQ files, and the subsequences that correspond to the adapters (including the barcodes) may be trimmed from the ends of the sequences. It will be appreciated that some sequencing errors may cause sequences to include barcodes that do not correspond to any sample, and, in an embodiment of the invention, such sequences may be disregarded.

This trimming may be performed, e.g., with a program such as fastq-mcf. fastq-mcf, which is available as open-source software as part of a package called ea-utils, may also use information that the sequencer provides about the quality of the reads to discard low-quality ends of sequences. In connection with an exemplary embodiment of the invention, fastq-mcf may be directed to discard read ends that have a quality score that is below 7.

(In connection with embodiments of the invention, the quality score may be, e.g., a PHRED score such as is known in the art. Put concisely, a PHRED score for a particular base position, after subtraction of a predetermined constant, is inversely proportional to the logarithm of the probability that the read at that position is incorrect.)

Once a patient's sequences have been transferred to the patient's individual FASTQ file, they may in block 530 be aligned to a reference genome, e.g., by a software package such as bwa, which is available as open source software. (In an embodiment of the invention, the reference genome may be a file that corresponds, e.g., to the Genome Reference Consortium human genome release 37 (GRCh37.1)). The aligned reads may be streamed to samtools, another open source software application, which may remove reads that do not pass a chastity filter (which filters reads that show high variation in read quality within a single sequence), sort the reads, and/or index the reads and store the aligned reads, e.g., in files using the BAM format. According to an embodiment of the invention, samtools may work with another software package (e.g., Picard, also available as open source) to create the BAM files.

Following alignment in block 530, in an embodiment of the invention, one or more cleanup steps may take place in block 540. For example, in an embodiment of the invention, applications such as GATK and Picard may, e.g., realign BAM files, remove duplicate reads, and/or recalibrate read quality scores, taking into account factors specific to the local implementation. The details of any cleanup in this step may depend, e.g., on the needs and details of a particular implementation.

In an embodiment of the invention, the aligned reads, stored, e.g., in BAM files, may be used in block 550 to determine gene dosages, as describe in more detail below. Finally, in block 560, the gene dosages and/or the presence or absence of any detected CNV may be reported.

Figure 6:
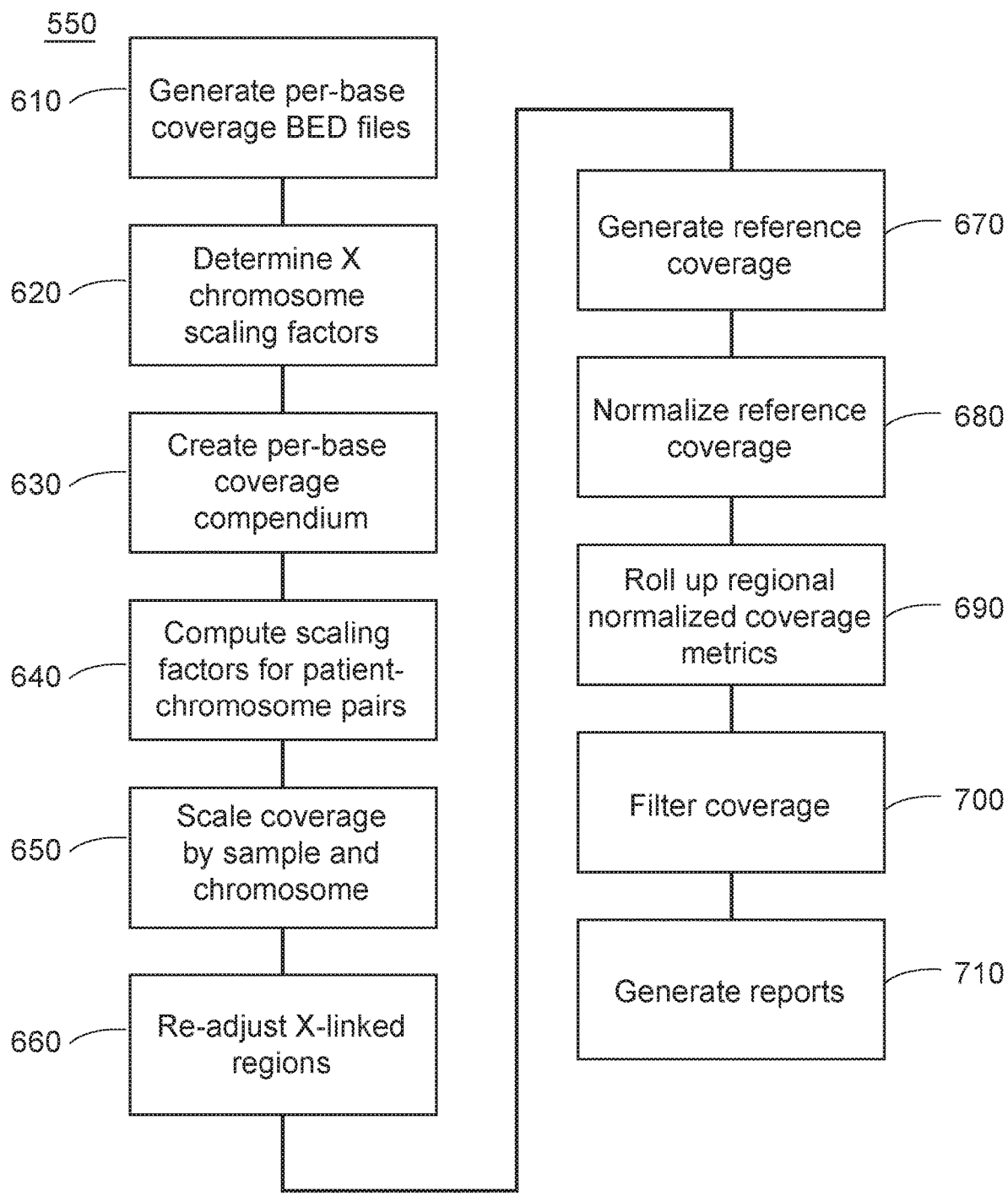
FIG. 6 depicts in more detail a flow of dosage analysis according to an embodiment of the invention.

FIG. 6 depicts the flow of dosage analysis 550 according to an embodiment of the invention. Dosage analysis 550 begins in block 610 with generating, for each sample, BED files that describe the coverage of each amplicon of interest. The data can be generated, e.g., by using the coverageBed application, which is part of the bedtools suite of open source software. coverageBed may take as input a BAM file that includes aligned reads for a patient and a BED file that describes each amplicon or other region of interest for which coverage information is desired. The output is a BED file that indicates the coverage in the sample of each amplicon or other region of interest, per base-pair position at which the amplicon or other region has been found.

"Coverage", in this context, refers to the number of times a feature was read during the sequencing run. Determining the coverage of any individual base may be relatively straightforward, requiring, e.g., only a count of the number of reads that include that base. It will be appreciated, however, that the number of nucleotides in an amplicon or other region may be orders of magnitude greater than the number of bases in any individual fragment that has been read. Moreover, fragments that overlap some or all of any amplicon or other region will begin and end at locations that vary from fragment to fragment.

It is therefore possible to define the coverage of a region in different ways. For example, the coverage of a region may be defined to be the arithmetic mean of the numbers of reads of the bases in the region, the median of those numbers, the largest of those numbers, or the smallest of them. It will be appreciated, however, that for very large numbers of reads, the differences between these values becomes relatively small, and similar results may be expected regardless of which of these definitions is chosen. In a preferred embodiment of the invention, however, "coverage" of a region refers to the arithmetic mean of the coverage of the bases within the region.

One significant source of normal variation in gene dosage is the sex-determination system: males normally have one X chromosome, and females normally have two. It may therefore be desirable in an embodiment of the invention to normalize the coverage of amplicons or other regions located on the X chromosome to account for the number of the patient's X chromosomes.

Determining that number may not be straightforward, though. A patient's sex may be incorrectly recorded on a laboratory requisition, for example. More fundamentally, though, a patient's karyotype may not be what is expected based on the patient's phenotype. In Klinefelter syndrome, for example, a person with a male phenotype may nonetheless have two X chromosomes.

Therefore, in block 620, an X-normalization factor may be computed for each patient. According to embodiments of the invention, the number of a patient's X chromosomes may be estimated by comparing the coverage of one or more X-linked amplicons or other regions with the coverage of one or more autosomal amplicons or other regions.

The comparison may take various forms. For example, in an embodiment of the invention, the comparison may rely simply on the ratio of the arithmetic mean coverage of X-linked amplicons to the arithmetic mean coverage of autosomal amplicons. If this ratio is near 0.5, the patient is determined to have a single X chromosome, and if it is nearer to 1.0, the patient is determined to have two X chromosomes. It is expected that ratios near the middle will be rare and most likely reflect errors.

Some conditions (e.g., trisomy X) may be associated with a patient's having more than two X chromosomes. It will be appreciated that such a condition would cause a different amplicon ratio to be seen. Embodiments of the invention variously may or may not account for this possibility.

In block 630, a compendium is assembled that includes the per-base coverage of all regions of interest for all samples. In an embodiment of the invention, data in the compendium may be grouped, e.g., by patient. For each patient, the coverage of X-linked regions may be adjusted based on the estimated number of the patient's X chromosomes: if the patient has only one X-chromosome, the recorded coverage of each X-linked region may be multiplied by two.

Block 640 represents computing patient-specific scaling factors for each of the 23 chromosome pairs. In an embodiment of the invention, this computation for a patient begins with computing a coverage estimate for each pair based on the coverage of regions known to be found on that pair. This number may be, e.g., the arithmetic mean of the coverage of the regions linked to that chromosome. The scaling factor for each chromosome may then be computed to be, e.g., the ratio of the mean coverage of the other 22 chromosomes to the mean coverage of the chromosome being scaled. Following calculation of the scaling factor for each of the chromosome, in block 650 the coverage of each region on that chromosome may be scaled, e.g., by multiplying the coverage by the chromosome-specific scaling factor.

(It will be recognized that, in connection with an embodiment of the invention, regions of interest may not exist in each of the 23 pairs of chromosomes. In connection with such an embodiment, the numbers of scaling factors and related quantities may be adjusted accordingly.)

In block 660, according to an embodiment of the invention, coverage of regions on the X chromosome may be adjusted again, based on the patient-specific scaling factor calculated for that patient's X chromosomes. For example, in an embodiment of the invention, original, unscaled coverage of all regions may be adjusted by the patient- and chromosome-specific scaling factors that were calculated in block 640. The ratio originally calculated in block 620 may then be recalculated based on the newly-scaled coverage, and then this ratio may be used to estimate the count of X chromosomes instead of the ratio computed earlier. If this recalculation results in a changed estimate of that count, then some or all of the scaling factors and scaled coverage numbers may be recalculated based on this new estimate.

Block 670 represents calculation of per-base reference coverage according to an embodiment of the invention. This reference coverage is calculated separately for each region, and the value calculated for each region is the expected coverage of that region from each patient. In an embodiment of the invention, the reference coverage for a particular region may be simply the mean coverage of that region across all patients. (Calculating the reference coverage in this way may reflect an assumption that samples will have comparable overall coverage consequent to the normalization of samples as part of pooling them, as described above.)

Block 680 represents normalization of copy numbers according to an embodiment of the invention. For example, in an embodiment, the normalized copy number may be the ratio of the sample coverage to the reference coverage calculated in block 670. This ratio may be rounded to the nearest integer to determine the likely dosage of that region.

Block 690 represents rolling up the per-base coverage into coverage by regions and generating coverage statistics for each patient's regions. For each region of each patient, "rolling up" the coverage of the region may include calculating, based on the coverage of the individual bases, the minimum coverage of any base in the region, the maximum coverage, and the mean coverage and standard deviation.

Rolling up may also comprise combining results for regions that are adjacent to each other in some sense and are judged to have the same dosages. For example, according to an embodiment of the invention, some or all regions of interest may correspond respectively to exons. Each region may subsume exactly one exon, extending slightly beyond one or both ends of the exon to ensure consistent coverage. If two adjacent exons have the same dosage, they may be rolled up together. (Exons may be considered adjacent for this purpose if they are normally joined to one another following removal of intervening introns.) When all exons in a gene have the same dosage, the dosages may be rolled up into a single dosage for the gene as a whole.

In an embodiment of the invention, analysis may comprise checking for the presence in the pool of ZFY, the gene that encodes zinc finger Y-chromosomal protein. If ZFY is present, analysis may also include computing the average coverage of ZFY for each individual patient and making a call of the presence or absence of ZFY in that patient.

It may be desirable to report CNV results for fewer regions than have been examined during the process, e.g., to avoid cluttering a report with information that may not be relevant to a current diagnostic process. Block 700 represents filtering out unrequested regions in an embodiment of the invention.

Figure 7:
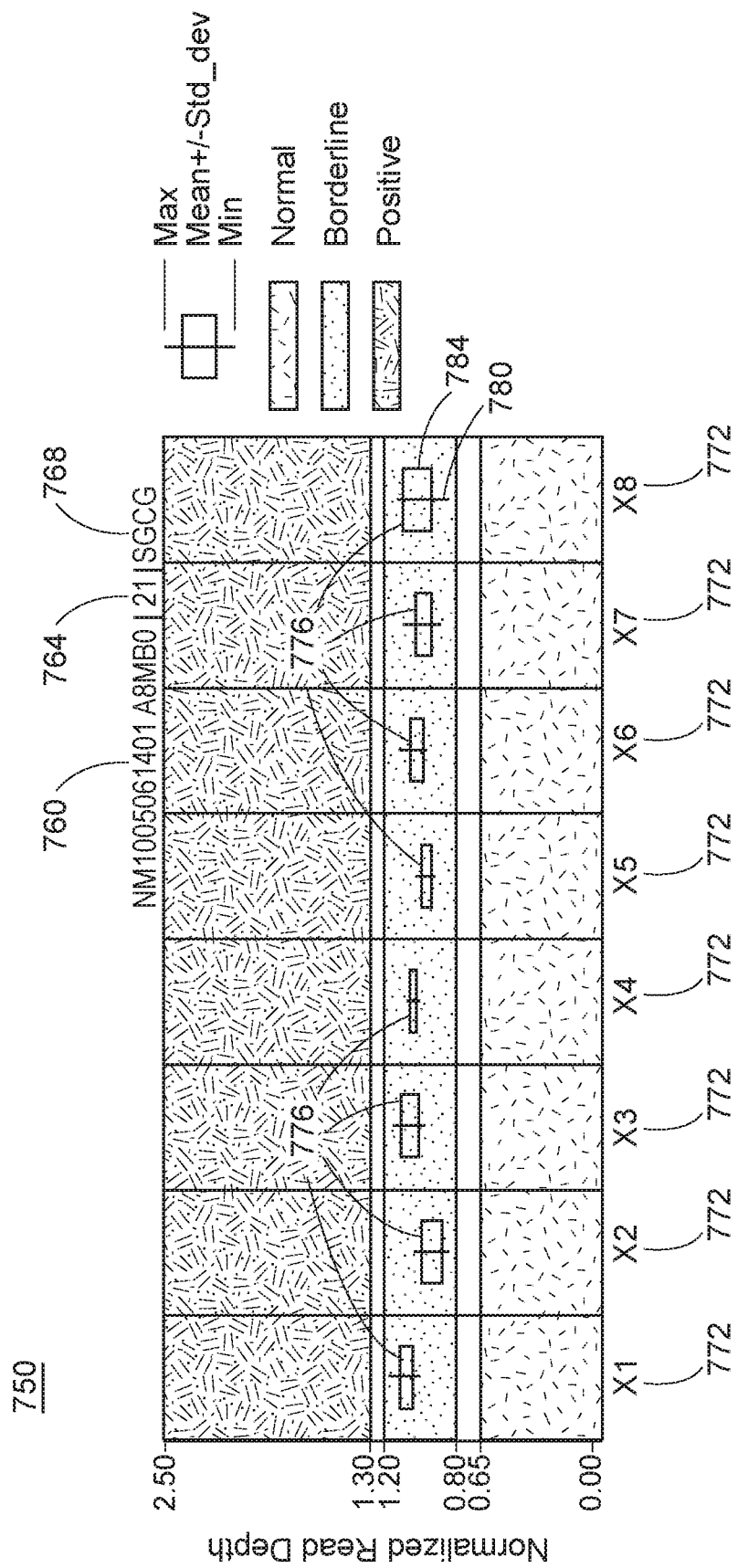
FIG. 7 depicts a plot of the results of DNA analysis according to an embodiment of the invention.

Finally, block 710 represents generating one or more reports based on the sequencing and subsequent analysis of the sequencing data. FIG. 7 depicts a sample plot 750 according to an embodiment of the invention. The plot 750 depicts normalized per-base coverage of eight exons that make up the SGCG gene. (Defects in SGCG, including duplication and deletion of exons, have been associated with a form of muscular dystrophy.) The plot 750 includes labels that indicate, e.g., the run ID 760 that generated the plotted statistics, the patient ID 764 (which may be unique only within a particular run), and the gene 768.

As depicted, the plot 750 presents statistics for each of the exons in SGCG. Labels 772 identify the exons associated with the respective values 776. For each exon, the extent of a vertical bar 780 indicates the minimum and maximum coverage of bases in the exon. A rectangle 784 superimposed on the bar 780 indicates a range of one standard deviation above and below the mean coverage. The depicted plot 750 indicates normal copy numbers for each exon, with each rectangle fully enclosed within a region between 0.8 and 1.2 times the expected coverage for bases within the exon.

Figure 8:
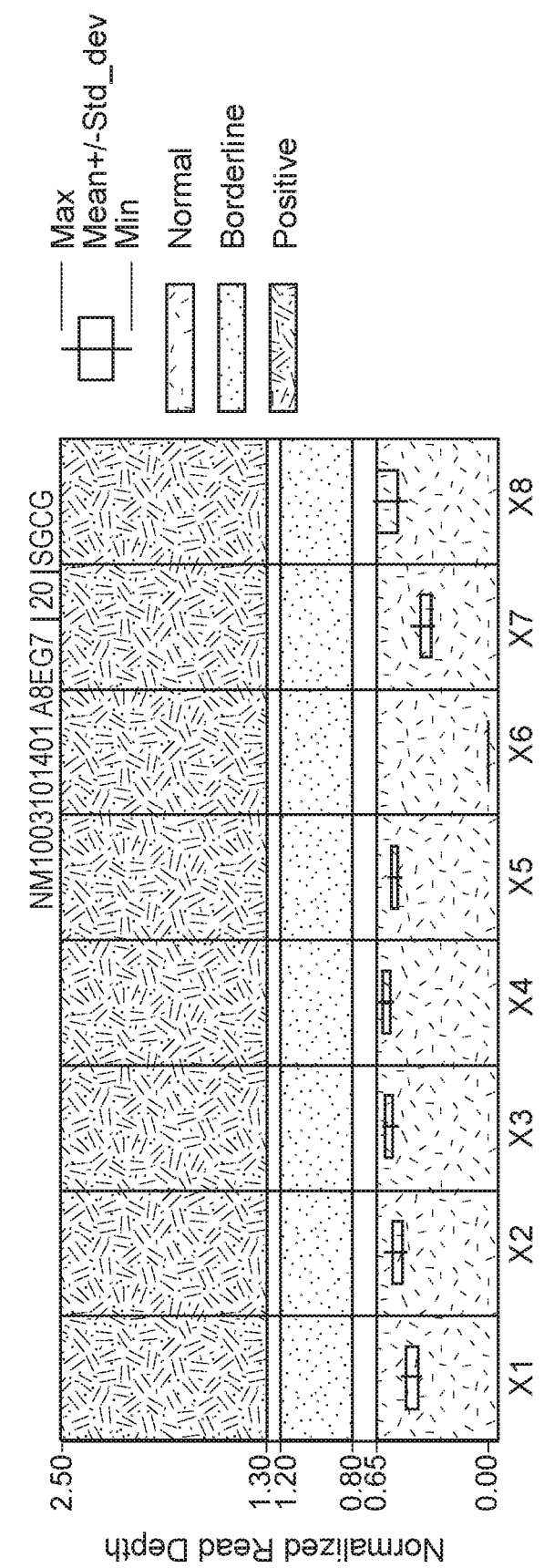
FIG. 8 depicts a second plot of the results of DNA analysis according to an embodiment of the invention.

FIG. 8 depicts a sample plot 800 that shows abnormal CNV in the SGCG gene. As depicted, the plot 800 indicates heterozygous deletion of exons 1-5 and 7-8 and homozygous deletion of exon 6.

The invention claimed is:

1. A method of detecting copy number variation (CNV) in the DNA of a plurality of patients, the method comprising:
   receiving a plurality of samples, each sample containing DNA from a single patient;
   from each sample, generating a plurality of fragments of DNA;
   barcoding each of the fragments with an identifier that uniquely identifies the respective patient from whom the DNA was received;
   pooling the plurality of samples into a DNA library;
   subjecting the DNA library to one or more stages of filtering to increase the relative concentration of fragments within a plurality of selected regions of interest;
   producing sequencing data for the plurality of patients by sequencing the filtered DNA library;
   demultiplexing the sequencing data;
   for each patient, generating coverage data by identifying, for each of the regions of interest, coverage of each region of interest in the sequencing data;
   generating normalized coverage data from the coverage data;
   generating reference coverage, common to all samples, for each region of interest, the generation of the reference coverage being based upon the normalized coverage data;
   automatically detecting CNV for at least one subsequence of at least one of the regions of interest of at least one of the patients based upon comparing the reference coverage to the normalized coverage data; and
   providing output that identifies the patient, the subsequence, and the CNV.

2. The method of claim 1, wherein generating normalized coverage data from the coverage data comprises:
   generating raw coverage data for each patient by at least generating an estimate of the number of the patient's X chromosomes based on the coverage data and scaling the patient's coverage of at least one region of interest that is known to be X-linked; and
   generating normalized coverage data from the raw coverage data.

3. The method of claim 2, wherein generating the estimate of the number of each patient's X chromosomes occurs without reference to any demographic information about the respective patient and without reference to any information about the respective patient's phenotype.

4. The method of claim 2, comprising:
   for each patient, generating a second estimate of the number of the patient's X chromosomes based on the normalized coverage data; and
   revising the normalized coverage data based on the second estimates.

5. The method of claim 4, wherein generating the second estimate of the number of each patient's X chromosomes occurs without reference to any demographic information about the respective patient and without reference to any information about the respective patient's phenotype.

6. The method of claim 2, wherein:
   the coverage data comprises per-base coverage for each region of interest within the sequencing data;
   generating raw coverage data comprises scaling the patient's per-base coverage of the at least one region of interest that is known to be X-linked;
   the normalized coverage data comprises per-base coverage;
   the reference coverage comprises per-base coverage for each position within each region of interest; and
   automatically detecting CNV is based upon the per-base reference coverage and the normalized coverage data.

7. The method of claim 1, wherein each region of interest corresponds respectively to exactly one exon and contains that exon.

8. The method of claim 7, comprising:
   automatically detecting CNV for a plurality of adjacent exons within a gene of a patient, each of the adjacent exons having the same CNV; and
   automatically rolling up the CNV of the adjacent exons.

9. The method of claim 8, comprising:
   automatically detecting CNV for all exons within a gene of a patient, each of the exons within the gene having the same CNV; and
   automatically rolling up the CNV of the exons within the gene into a single CNV for the gene.

10. The method of claim 7, comprising subjecting the DNA library to one or more stages of amplification, such that each region of interest is an amplicon.

11. The method of claim 1, wherein:
the coverage data comprises per-base coverage for each region of interest within the sequencing data;
the normalized coverage data comprises per-base coverage;
the reference coverage comprises per-base coverage for each position within each region of interest; and
automatically detecting CNV is based upon the per-base reference coverage and the normalized coverage data.

12. A method of detecting copy number variation (CNV) in one or more regions of respective X chromosomes of a plurality of patients, the method comprising:
receiving a plurality of samples, each sample containing DNA from a single patient;
from each sample, generating a plurality of fragments of DNA;
barcoding each of the fragments with an identifier that uniquely identifies the respective patient from whom the DNA was received;
pooling the plurality of samples into a DNA library;
subjecting the DNA library to one or more stages of filtering to increase the relative concentration of fragments within a plurality of selected regions of interest, at least one of the selected regions of interest being a region known to exist within the X chromosome;
producing sequencing data for the plurality of patients by sequencing the filtered DNA library;
demultiplexing the sequencing data;
for each patient, generating coverage data by identifying, for each of the regions of interest, coverage of each region of interest in the sequencing data;
generating normalized coverage data from the coverage data;
generating reference coverage, common to all samples, for each region of interest, the generation of the reference coverage being based upon the normalized coverage data;
automatically detecting CNV for at least one subsequence of at least one of the regions of interest of at least one of the patients based upon comparing the reference coverage to the normalized coverage data, at least one of the at least one subsequences being within the region known to exist within the X chromosome; and
providing output that identifies the patient, at least one of the subsequences within the region of interest known to exist within the X chromosome, and the CNV of the at least one of the subsequences within the region of interest.

* * * * *

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: This sequence was arbitrarily selected to
      illustrate the meaning of blunting and may lack any special
      biological significance

<400> SEQUENCE: 1
agtcgatcgt tttgtagtag ctgt                                          24

<210> SEQ ID NO 2
<211> LENGTH: 16
<212> TYPE: DNA

```
<213> ORGANISM: Artificial Sequence
<220> FEATURE:
<223> OTHER INFORMATION: This sequence was arbitrarily selected to
      illustrate the meaning of blunting and may lack any special
      biological significance

<400> SEQUENCE: 2
gctactacaa aacgat                                                        16

<210> SEQ ID NO 3
<211> LENGTH: 21
<212> TYPE: DNA
<213> ORGANISM: Artificial Sequence
<220> FEATURE:
<223> OTHER INFORMATION: This sequence was arbitrarily selected to
      illustrate the meaning of blunting and may lack any special
      biological significance

<400> SEQUENCE: 3
gctactacaa aacgatcgac t                                                  21
```